United States Patent
Panus

(10) Patent No.: US 11,013,588 B2
(45) Date of Patent: May 25, 2021

(54) TISSUE HEART VALVE (THV) HUMIDOR PACKAGING SYSTEM

(71) Applicant: St. Jude Medical, Cardiology Division, Inc., St. Paul, MN (US)

(72) Inventor: David A. Panus, Maple Grove, MN (US)

(73) Assignee: St. Jude Medical, Cardiology Division, Inc., St. Paul, MN (US)

( * ) Notice: Subject to any disclaimer, the term of this patent is extended or adjusted under 35 U.S.C. 154(b) by 476 days.

(21) Appl. No.: 15/816,043

(22) Filed: Nov. 17, 2017

(65) Prior Publication Data

US 2018/0140411 A1     May 24, 2018

Related U.S. Application Data

(60) Provisional application No. 62/425,654, filed on Nov. 23, 2016.

(51) Int. Cl.

| | |
|---|---|
| *A61F 2/00* | (2006.01) |
| *B65B 5/04* | (2006.01) |
| *B67B 3/20* | (2006.01) |
| *A61F 2/24* | (2006.01) |
| *A61L 2/00* | (2006.01) |

(52) U.S. Cl.
CPC .......... *A61F 2/0095* (2013.01); *A61F 2/2412* (2013.01); *A61F 2/2415* (2013.01); *A61L 2/0088* (2013.01); *A61L 2/0094* (2013.01); *B65B 5/04* (2013.01); *B67B 3/20* (2013.01); *A61L 2202/21* (2013.01)

(58) Field of Classification Search
CPC . B65D 85/30; A61F 2/24; A61B 17/06; A61L 2202/21; A61L 2209/00

USPC ................................................. 206/210, 438
See application file for complete search history.

(56) References Cited

U.S. PATENT DOCUMENTS

| | | | | |
|---|---|---|---|---|
| 4,765,499 A | * | 8/1988 | von Reis | ............ B65D 51/1616 215/261 |
| 7,389,874 B2 | * | 6/2008 | Quest | .................... A61F 2/2427 206/210 |

(Continued)

FOREIGN PATENT DOCUMENTS

WO     9836992 A1     8/1998

OTHER PUBLICATIONS

International Search Report for Application No. PCT/US2017/062191 dated Feb. 12, 2018.

*Primary Examiner* — Anthony D Stashick
*Assistant Examiner* — Raven Collins
(74) *Attorney, Agent, or Firm* — Lerner, David, Littenberg, Krumholz & Mentlik, LLP

(57) ABSTRACT

A prosthetic valve packaging system includes a jar, a lid, a lid liner, and a humectant. The jar has a closed end, an open end, a side wall and an interior sized to receive the prosthetic heart valve. The lid is connected to the open end of the jar. The lid liner includes a rim sandwiched between the lid and the side wall of the jar to provide a fluid-tight seal. The humectant is supported within the interior of the jar. The humectant may be supported by the lid liner. The lid liner may include one or more windows so that the humectant may provide a desired humidity to the inside of jar to maintain a desired water content in the tissue of the valve. The system may obviate the need to store the valve in a dry state, or to otherwise store the valve submerged in an aldehyde solution.

5 Claims, 6 Drawing Sheets

(56) References Cited

U.S. PATENT DOCUMENTS

| | | | |
|---|---|---|---|
| 2003/0015465 A1* | 1/2003 | Fick | B01D 35/153 |
| | | | 210/234 |
| 2007/0061008 A1 | 3/2007 | Salahieh et al. | |
| 2013/0325111 A1 | 12/2013 | Campbell et al. | |
| 2014/0311345 A1* | 10/2014 | Morrissette | B65D 81/245 |
| | | | 96/11 |
| 2014/0328939 A1* | 11/2014 | Kim | A61L 27/52 |
| | | | 424/551 |
| 2017/0233140 A1* | 8/2017 | McMunn | B65D 25/14 |
| | | | 220/228 |

\* cited by examiner

TISSUE HEART VALVE (THV) HUMIDOR PACKAGING SYSTEM

CROSS-REFERENCE TO RELATED APPLICATIONS

This application claims the benefit of the filing date of U.S. Provisional Patent Application No. 62/425,654 filed on Nov. 23, 2016, the disclosure of which is hereby incorporated by reference herein.

BACKGROUND OF THE DISCLOSURE

The present disclosure relates to prosthetic heart valves, and more particularly, to a system and method for packaging and shipping prosthetic heart valves in a sterilized and hydrated condition.

Heart valve diseases continue to be a significant cause of morbidity and mortality. Currently, a treatment for heart valve diseases is valve replacement. Bioprosthetic heart valves, which are also generally known as tissue heart valves ("THVs"), are commonly used to replace damaged or diseased native heart valves. THVs may utilize biologically derived tissue, such as porcine or bovine tissue, to fabricate flexible fluid-occluding leaflets.

To prevent the transmission of disease-causing microorganisms to the heart valve recipient, THVs are conventionally packaged in jars filled with a preserving solution for shipping and storage prior to use. To minimize the possibility of damage to relatively delicate tissue valves, THVs are usually stabilized with a bracketing structure to prevent them from striking the inside of the jar. A nurse or surgeon may have to reach into the preserving solution to retrieve the tissue valve and then remove the bracketing structure. This may cause contamination of the gloves of the person retrieving the tissue valve.

Glutaraldehyde and formaldehyde are widely used as preserving solutions due to their sterilization properties. These solutions help keep the tissue in a hydrated state and kill any microbes that may be attached to the tissue. However, both glutaraldehyde and formaldehyde are irritants and have some inherent level of toxicity. They are also known to contribute to calcification of THVs and subsequent tearing of the valve leaflets. A THV that is stored in such a solution therefore may require extensive rinsing to remove any residual aldehydes prior to implantation in a patient.

To eliminate the preserving solution in the THV packaging system, one strategy is to dehydrate the bioprosthetic tissue, sterilize the dry tissue, and package the final product "dry." To effect this strategy, several processes including chemical dehydration using glycerin, alcohols, or combinations thereof, or physical dehydration by air drying or freeze-drying (also known as "lyophilization") may be implemented so that the resulting tissue is in a "dry" state. The dry tissue may be sterilized using ethylene oxide, gamma irradiation, or electron beam irradiation, and then packaged as a final product. Since dry THVs do not need to be shipped or stored in a solution to prevent the tissue from drying out, they may be pre-loaded onto delivery devices, with the entire assembly being provided in sterile packaging such that the valves are able to be reconstituted either before use or potentially in situ (in the patient) by blood or other fluid in the patient's body (i.e., biofluid) during implantation. However, dehydration can affect the tissue dimensions and properties, and lead to a compromised structure-to-function relationship between the tissue and valve performance and durability.

Therefore, it would be desirable to develop a THV packaging system which provides adequate humidity to maintain the tissue valve in a properly hydrated form without the need to submerge the tissue valve in aldehyde solutions and without the need to store the tissue in a dehydrated form.

BRIEF SUMMARY

According to one aspect of the disclosure, a prosthetic valve packaging system includes a jar, a lid, a lid liner, and a humectant. The jar has a closed end, an open end, a side wall, and an interior sized to receive a prosthetic valve therein. The lid is connected to the open end of the jar and the lid liner has a rim sandwiched between the lid and the side wall of the jar. The humectant is supported within the interior of the jar.

According to another aspect of the disclosure, a method of packaging a prosthetic valve in a packaging system includes providing a jar having a closed end, an open end, a sidewall and an interior. The prosthetic valve may be positioned within the interior of the jar, and a humectant may be positioned within the interior of the jar. A lid may be connected to the jar to close the open end of the jar. The prosthetic valve is not submerged in a storage solution when the lid is connected to the jar.

BRIEF DESCRIPTION OF THE DRAWINGS

These and other features, aspects, and advantages of the present disclosure will become better understood with regard to the following description, appended claims, and accompanying drawings in which:

DETAILED DESCRIPTION

The present disclosure relates to a packaging system for a prosthetic heart valve that effectively stabilizes the tissue of the prosthetic valve during storage by maintaining an adequate level of humidity for the tissue within the final packaging container without the need for the prosthetic valve to be submerged in a storage solution, such as an aldehyde solution. The packaging system may also provide an efficient vehicle for sterilization.

Bioprosthetic valves, which are also generally known as "tissue valves," are made with tissue of biological origin. "Biological tissue" or "tissue" as used herein refers to biological tissue originating from an animal such as, for example, porcine or bovine tissue, or tissue of other species. Specific tissue types that may be used include, without limitation, any blood vessel, pericardial tissue, heart muscle tissue, dura mater and the like. Prosthetic tissues that mimic or approximate the properties of biological tissue may also be referred to as "biological tissue" or "tissue." More than one species and tissue type may be used in a valve assembly. The term "valve" as used herein refers to a structure capable of being implanted into a patient to control the flow of blood through the patient's circulatory system. A valve can be a surgical valve, a transcatheter valve or any other non-native valve structure. The terms "implanted" and "implantation" as used herein refer to a substantially complete and long-term seating of a valve in a patient. A "valve assembly" as used herein is a structure that is made, at least in part, from tissue, and that operates to meter or restrict blood flow for at least some period of time, but does not include other structures like a stent often used to support the valve assembly. Thus, a tissue valve for purposes of the present description is a bioprosthetic valve that includes at least a valve assembly. The tissue valve may, and often does, include other structures, such as a supporting stent. Bioprosthetic valves in accordance with the present disclosure may be used in the heart as a replacement for one of the native cardiac valves, such as the aortic valve or mitral valve. But the bioprosthetic valves herein are not limited thereto and can be used in other structures, including blood vessels.

Figure 1:
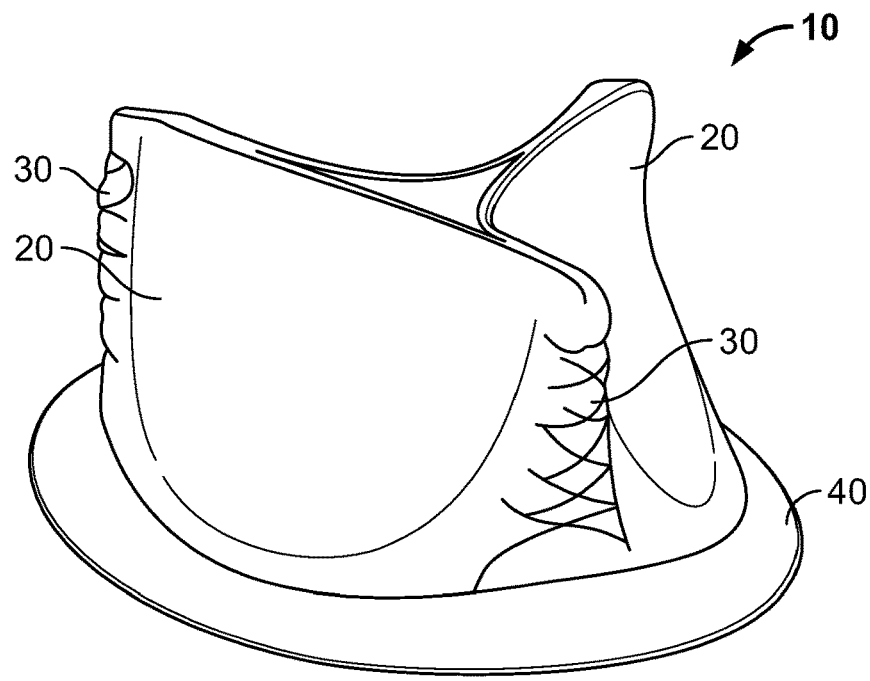
FIG. 1 is a top perspective view of a prosthetic heart valve according to the prior art.

FIG. 1 illustrates a prosthetic aortic heart valve 10 according to the prior art to be used as a replacement for an excised native heart valve of a patient. The valve 10 includes a plurality of leaflets 20. Although a tricuspid valve is illustrated in FIG. 1, other configurations, such as bicuspid valves, may be used to replace a native heart valve. The leaflets 20 may be connected to a stent that provides structural support to the leaflets. For example, each leaflet 20 may be attached to commissure posts 30 extending generally axially from a base of the stent. In the valve 10 illustrated in FIG. 1, the leaflets 20 are positioned externally of the stent. In other valves, the leaflets 20 may be positioned internally of the stent.

A suture ring or sewing cuff 40 may be attached to the stent and/or valve 10 at an inflow end of the valve. The sewing cuff 40 is used to attach the valve 10 to the patient's heart tissue. The leaflets 20 may open at an outflow end to allow blood to flow through the valve in the antegrade direction, and coapt with one another to prevent blood from flowing back through the valve in the retrograde direction.

It should be understood that valve 10 is merely one example of a tissue heart valve that may be stored in the packaging system of the present disclosure. For example, in one embodiment, a prosthetic valve to be stored in the packaging system of the present disclosure may be a wet tissue valve which is removed from an aqueous aldehyde solution containing about 0.05-10 wt % of glutaraldehyde or formaldehyde and optionally rinsed with a sterile saline solution. In another embodiment, a prosthetic valve to be stored in the packaging system of the present disclosure may be a dried tissue valve prepared by conventional methods known to one of ordinary skill in the art. These methods may dry the valve tissue, such as through the use of glycerin, alcohols, and/or combinations thereof, through air drying, or through lyophilization.

Figure 2:
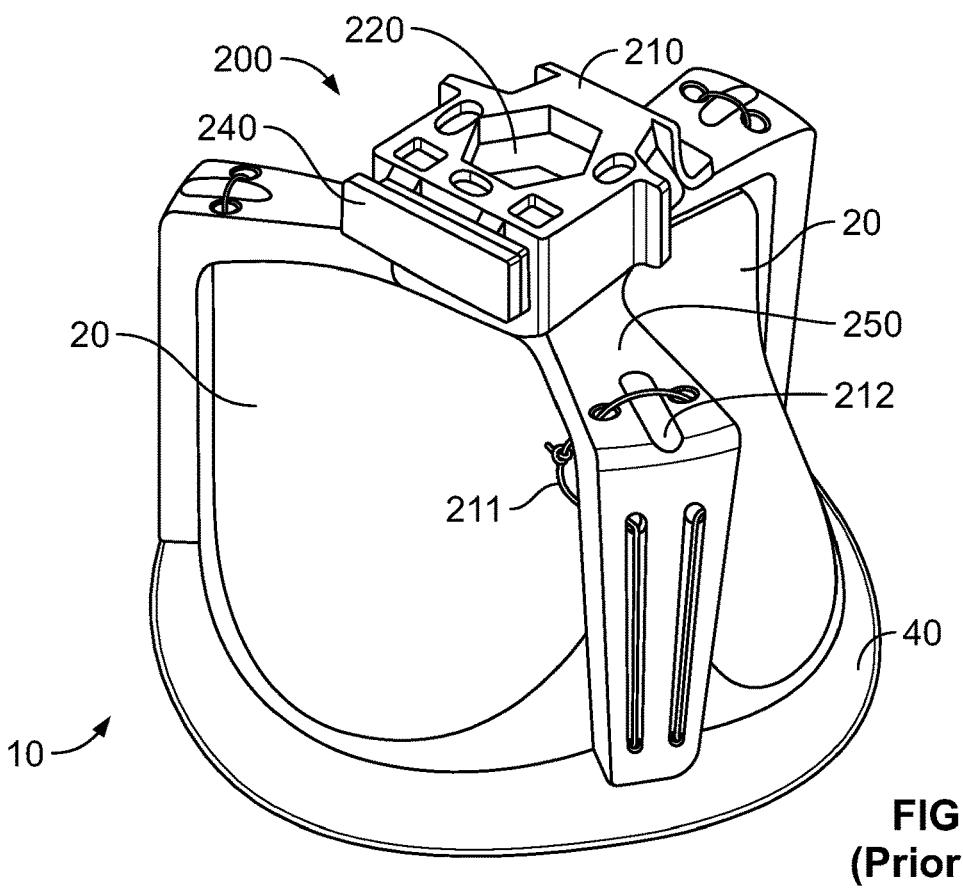
FIG. 2 is a top perspective view of a valve holder according to the prior art coupled to the valve of FIG. 1.

An embodiment of a valve holder 200 according to the prior art is illustrated in FIG. 2 attached to valve 10. Valve holder 200 is intended to hold a surgical valve in place and generally includes a base 210 with an aperture 220 shaped to accept the shaft of an elongated handle (not shown). The handle may be coupled to the valve holder 200 in order to remove the valve 10 from a storage container, and also to facilitate a surgeon in placing the valve 10 in a desired position and orientation during implantation. The base may also include a locking mechanism 240 to lock the shaft of the handle into base 210. Depressing the locking mechanism 240 releases the shaft from the base 210 of the valve holder 200. Three fingers 250 extend radially outwardly from the base 210 and then downward generally parallel to a longitudinal axis of the valve 10. The fingers 250 are spaced from one another so as to correspond to the positions of commissure posts 30 of valve 10. Therefore, when the valve holder 200 is coupled to valve 10, fingers 250 will abut the commissure posts 30. This relative position of the fingers 250 with respect to the leaflets 20 may help protect the leaflets 20 during storage, for example by preventing direct contact with a wall of the storage container. The fingers 250 may also serve to constrict the commissure posts 30 radially inwardly, which may reduce the necessary size of the container, and also provide better visibility to the surgeon during implantation of the valve 10. The fingers 250 may be sutured to the valve 10 to fix the holder 200 in place relative to the valve. A suture 211 may pass across a groove 212 in the top of finger 250, through apertures in the top and side of the finger, and across the sewing cuff 40. The groove 212 allows a surgeon to easily cut the suture 211 when desired with a scalpel or other tool, by sliding the scalpel across the suture at the location of the groove.

It should be understood that valve holder 200 is merely one example of a valve holder that may be used in combination with a tissue heart valve to be stored in the container of the present disclosure. For example, a valve holder used with a prosthetic mitral valve may be coupled to a sewing ring of that valve, with the leaflets and commissures of the mitral valve extending away from the valve holder. In such embodiments, additional components may be provided to protect the leaflets of the valve during storage. Similarly, different valve holders, or no valve holders at all, may be used to help stabilize collapsible and expandable heart valves within the packaging system of the present disclosure. Additional examples of valve holders are described in greater detail in U.S. Pat. No. 7,389,874, the disclosure of which is hereby incorporated by reference herein.

Figure 3:
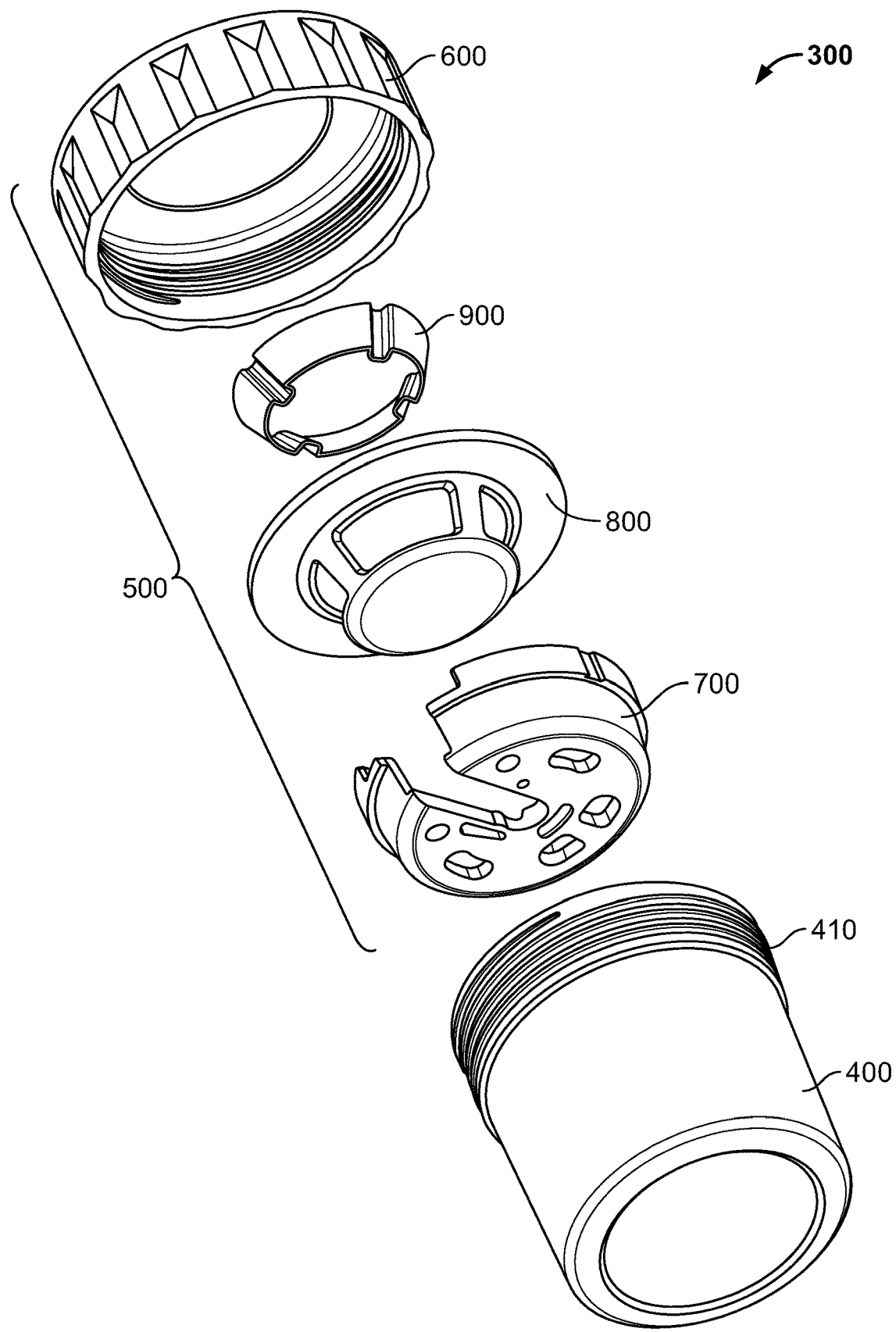
FIG. 3 is an exploded perspective view of one exemplary tissue humidor packaging system according to the present disclosure.
Figure 4:
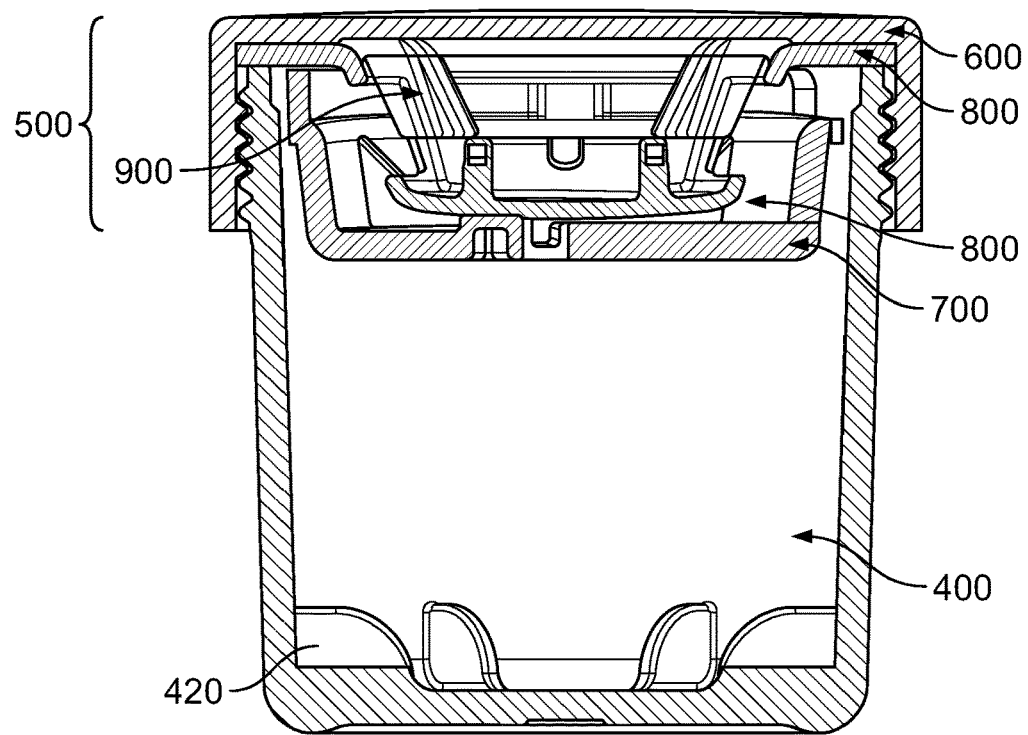
FIG. 4 is a longitudinal cross-sectional view of the tissue humidor packaging system of FIG. 3.

FIG. 3 is an exploded view of one embodiment of a tissue heart valve humidor packaging system 300 according to the teachings of the present disclosure. FIG. 4 is a longitudinal cross-sectional view of the tissue humidor packaging system 300 of FIG. 3. In the illustrated embodiment, packaging system 300 includes jar 400 and lid assembly 500 which can be secured to each other tightly to form a sterile sealed container to store and transport prosthetic valve 10 assembled to valve holder 200, although it should be understood that other valves and/or other valve holders may be used with packaging system 300.

Jar 400 may be dimensioned for storing prosthetic valve 10, which is preferably but not necessarily assembled to valve holder 200. When valve holder 200 is assembled to prosthetic valve 10 and positioned within packaging system 300, sewing cuff 40 may be positioned near the bottom of jar 400 with valve holder 200 positioned between the prosthetic heart valve 10 and the lid 600 of packaging system 300. However, it should be understood that additional support members may be provided with prosthetic heart valve 10 to protect sewing cuff 40 or other portions of prosthetic heart valve 10 from contacting jar 400. Further, the orientation of a prosthetic heart valve contained within packaging system 300 may depend on the type of valve. For a mitral valve, a valve holder may be coupled to or otherwise engage a sewing ring of the mitral valve, with the leaflets of the valve extending down toward the bottom of jar 400, and the sewing ring being positioned between the leaflets and the valve holder. Any additional supports may be included to aid in securing the prosthetic heart valve in a desired fashion in packaging system 300.

Jar 400 may be formed of any material suitable for storing tissue valves, including, but not limited to, plastics (e.g., polyolefins, polyamides, polyesters, silicones, polyurethanes, epoxies, acrylics, polyacrylates, polyesters, polysulfones, polymethacrylates, PEEK, polyimide and fluoropolymers) and glass products including silica glass. Preferably, jar 400 is transparent. Examples of suitable transparent thermoplastic materials for jar 400 include, for example, polycarbonates, polyethylene, polypropylene and polyethyleneterephthalate. Plastic materials can be air impermeable materials or may contain an air impermeable or semi permeable layer.

Figure 5:
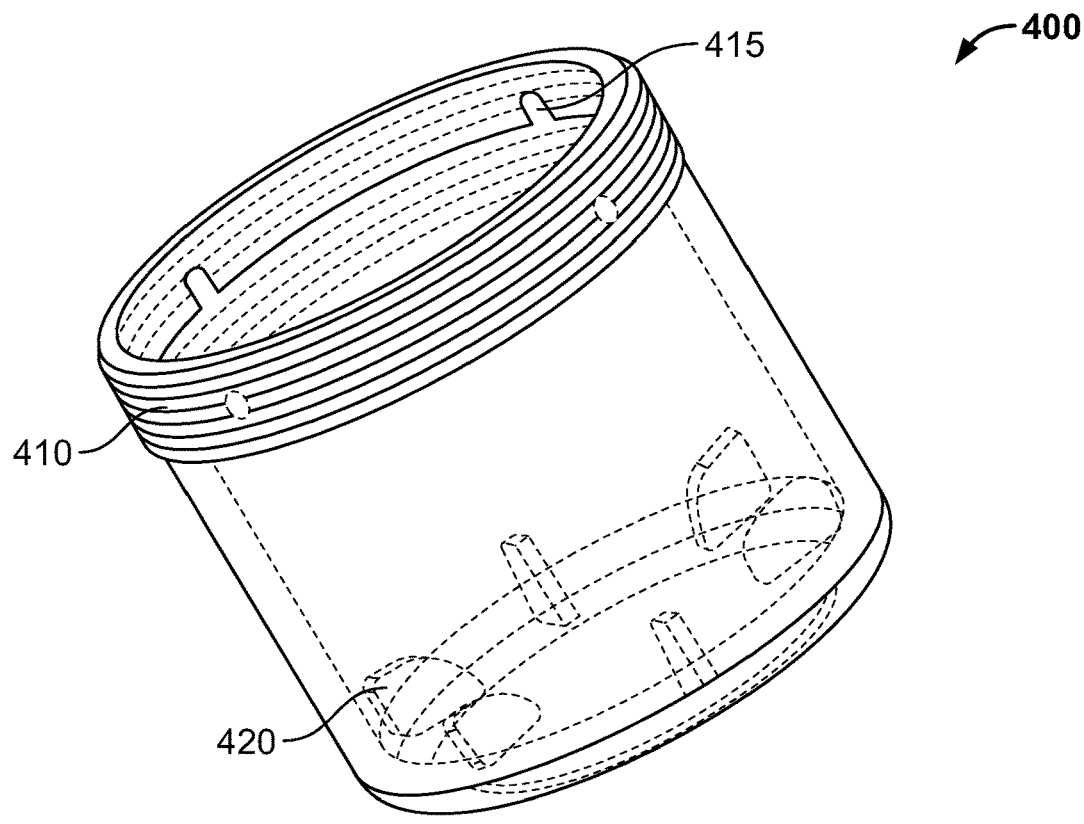
FIG. 5 is an isometric view of the jar of the packaging system of FIG. 3.
Figure 6:
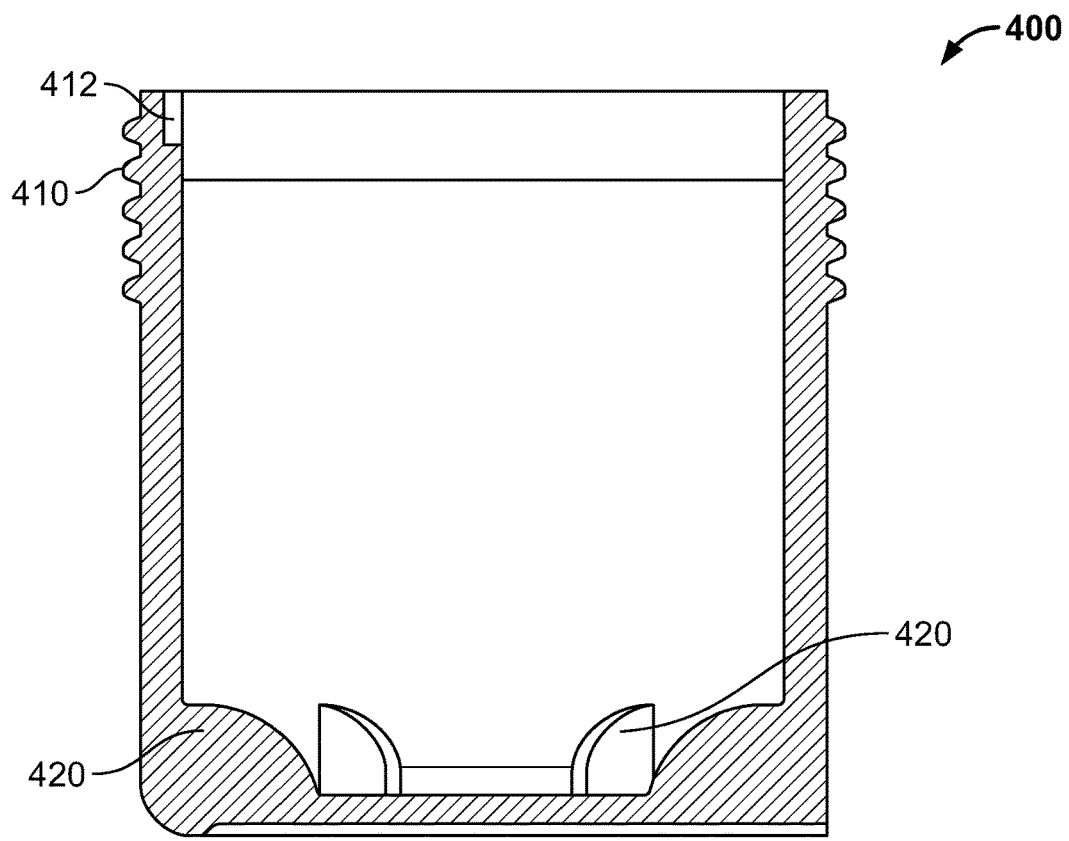
FIG. 6 is a longitudinal cross-section of the jar of FIG. 5.

Jar 400 is illustrated isolated from the remainder of packaging system 300 in FIGS. 5-6. In the illustrated embodiment, jar 400 is a substantially hollow cylinder with a closed bottom end and an open top end. The top end of jar 400 may include threads 410 or other mating features to engage with corresponding threads or other mating features of the lid 600. Jar 400 may also include a plurality of tabs 420. In the illustrated embodiment, tabs 420 are thin structures connecting the bottom of jar 400 to the side wall of the jar. Tabs 420 may be positioned a spaced distance from one another in a circumferential direction around the bottom of jar 400, for example with equal spacing. Tabs 420 may function to interact with one or more members of a support device supporting the prosthetic heart valve within jar 400 in order to prevent rotation of the prosthetic heart valve and the support(s) to which it is coupled. It should be understood that in some embodiments, tabs 420 may be absent from jar 400, and rotation of the valve and/or valve holder relative to the jar may be prevented by other means, such as through a connection with collar 700 or an alternate support device serving a similar function as the collar, as will be explained below.

Referring again to FIG. 3, lid assembly 500 may include lid 600, collar 700, a lid liner 800, and a humectant 900. Lid 600 may be dimensioned to fit over the outside of jar 400 and may include internal threads or other mating features to engage with corresponding mating features, such as threads 410, of jar 400. Lid 600 may be formed of any suitable materials, including, for example, polypropylene.

Figure 7:
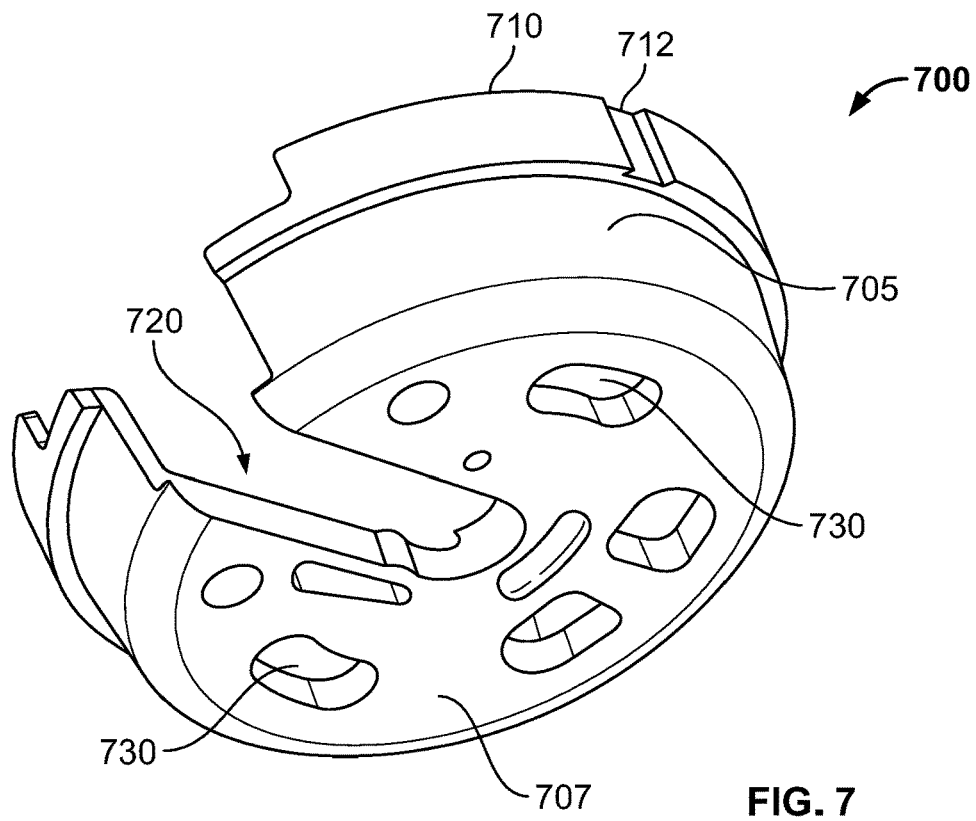
FIG. 7 is a perspective view of a bottom of the valve collar of the packaging system of FIG. 3.

Valve collar 700 is shown in FIG. 7. It should be understood that valve collar 700 may be designed specifically for valve 10 and/or valve holder 200, and alternate support devices that serve the same or similar function as the illustrated valve collar may be provided for different types of heart valves. In other words, in some embodiments, one or more alternate valve supports specific to the valve being stored in packaging system 300 may be used in the place of valve collar 700, with or without a valve holder. Valve collar 700 may be substantially cylindrical with an annular sidewall 705, an open top and a partially closed bottom 707. The top of side wall 705 may include an annular rim 710 extending radially outward a distance farther than the side wall. Referring back to FIG. 6, a portion of the inner wall of jar 400 may form a circumferential recess that defines at least one shoulder 412. The rim 710 of valve collar 700 may be dimensioned to extend into the recess of jar 400 so as to rest on shoulder 412. The rest of side wall 705 below rim 710 may have a diameter that is slightly less than the inside diameter of jar 400 below shoulder 412. With this configuration, valve collar 700 may snugly fit within jar 400, with the valve collar being suspended by the interaction between rim 710 and shoulder 412. The smooth annular shape of rim 710 may be interrupted by one or more recesses 712. One or more ribs 415 may project upwardly from shoulder 412 at spaced locations around the circumference of jar 400 and may project radially inward from the inner side wall at the top of the jar until substantially flush with the remainder of the inner side wall of the jar. With valve collar 700 properly aligned in the circumferential direction with jar 400, ribs 415 will fit within recesses 712 in the rim 710 of the valve collar to prevent the valve collar from rotating when assembled to the jar 400.

Valve collar 700 may also include a slot 720 extending partially through the bottom 707 of valve collar 700 along a radius thereof, and also interrupting the side wall 705 of the valve collar including rim 710. Preferably, slot 720 is dimensioned to correspond to dimensions of a portion of a valve holder, such as base 210 of valve holder 200, so that the valve holder may be slidingly received in the slot. More particularly base 210 preferably is undercut so as to have a neck portion (not shown) that is just narrower than the width of slot 720 and a head that is wider than the width of slot 720. As a result, when valve holder 200 is assembled to the slot 720 of valve collar 700 the valve holder will be suspended from the valve collar. Slot 720 may also include other mating or locking features corresponding to valve holder 200 in order to provide a secure fit between the valve holder and the collar 700, for example to prevent unintentional rotation of the valve holder as well as other movement, such as unintentional sliding movement, of the valve holder with respect to the collar during storage, handling, and/or transport. It should be understood that although the valve and valve holder may be suspended from valve collar 700, portions of the valve holder or the valve may be in contact with the bottom and/or side walls of jar 400, with or without additional support members, to vertically stabilize the valve and valve holder while stored in packaging system 300. In some systems, valve collar 700 may be partially or entirely replaced with a different type of valve support, for example one which sits at the bottom of jar 400 and has features that stabilize the valve within the packaging system 300. Valve collar 700 may also include one or more apertures 730 in bottom 707. Apertures 730 may function to allow fluid communication between the inside of jar 400 below valve collar 700 and the region above valve collar 700 when the valve collar is assembled to the jar. As will become clear, these apertures 730 may permit humidity above valve collar 700 in packaging system 300, such as from a humectant 900 disposed in lid assembly 500, to surround the prosthetic valve 10 positioned below the valve collar and maintain it in a hydrated condition. Apertures 730 may also enable the prosthetic valve 10 to be sterilized while positioned in jar 400 below collar 700.

Figure 8:
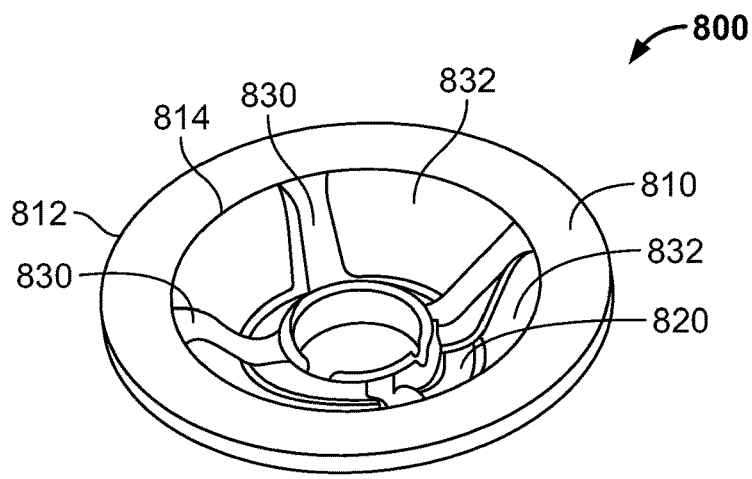
FIG. 8 is a top perspective view of the lid liner of the packaging system of FIG. 3.
Figure 9:
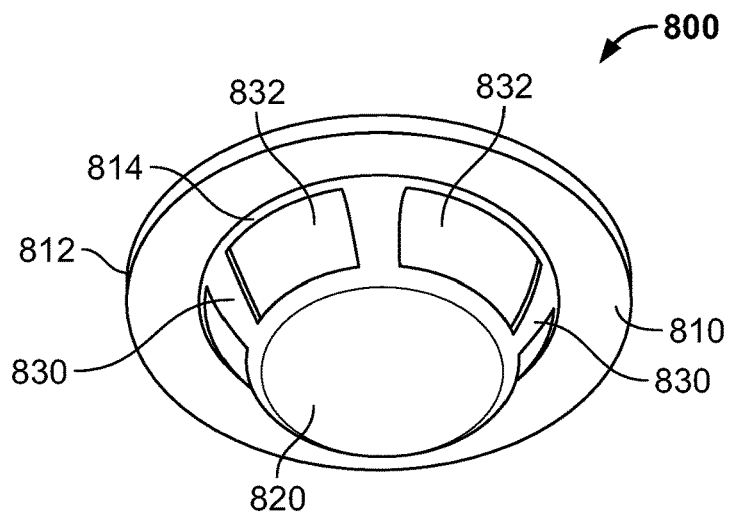
FIG. 9 is a bottom perspective view of the lid liner of FIG. 8.

Lid liner 800 is shown in greater detail in FIGS. 8-9. Lid liner 800 may be formed of any suitable material, including silicone, synthetic rubbers, thermoset plastics, certain thermoplastics, or other elastomers. Lid liner 800 may include a top rim 810 having a substantially flat annular shape defined, at least in part, by an outer rim edge 812 and an inner rim edge 814. The top rim 810 may be dimensioned so that, when placed on jar 400, the outer rim edge 812 is substantially flush with the outer wall of the top open end of jar 400. It should be understood that, with this configuration, the top rim 810 may rest on the top of the side wall of jar 400 and may also at least partially rest on the top of valve collar 700 when the valve collar is assembled to the jar. Further, lid 600 may be screwed onto (or otherwise engaged with) jar 400 so that a portion of the top rim 810 of lid liner 800 is sandwiched between the lid and the jar, providing for fluid-tight sealing of packaging system 300.

Lid liner 800 may have a bottom support surface 820 adapted to be positioned closer to the bottom of jar 400 when the components are in an assembled state. Support surface 820 may be substantially circular and may be positioned with respect to top rim 810 so that a longitudinal axis passing through the center of outer rim 810 also passes through the center of support surface 820. When a valve holder is assembled to valve collar 700, and lid liner 800 is positioned between lid 600 and the valve collar, the support surface 820 of the lid liner may abut the portion of the valve holder extending above the valve collar through slot 720. If the lid liner 800 is formed of an elastomer or other similarly compressible material, the support surface 820 of the lid liner may deform to some degree about the portion of the valve holder it contacts, providing additional stability to the valve holder in the packaging system 300.

The support surface 820 of lid liner 800 may be connected to outer rim 810 by a plurality of struts 830 that are circumferentially spaced from one another. In the illustrated embodiment, each of four struts 830 has a first end connected to the inner rim edge 814 and a second end connected to an edge of the support surface 820 of lid liner 800. The struts 830 extend downwardly and radially inwardly from outer rim 810 toward support surface 820. This configuration defines four windows 832 in lid liner 800, each window 832 being positioned between two circumferentially adjacent struts 830. Although windows 832 are shown with a substantially rectangular shape, depending on the shape, positions and orientations of struts 830, lid liner 800 may have windows of an shape, including but not limited to circular, oval, square or combinations thereof. Moreover, the shapes and sizes of struts 830, windows 832 and recesses 940 need not all be the same, and in in any single humectant 900 and lid liner 800 there may be a combination of shapes and sizes In addition to creating a fluid tight seal between lid 600 and jar 400, lid liner 800 may function as a support for humectant 900, shown in FIG. 10, so that the humectant is supported within the lid of the jar. As shown in FIG. 3, humectant 900 may be positioned between support surface 820 of lid liner 800 and lid 600 when packaging system 300 is in the assembled condition. Referring back to FIG. 10, humectant 900 may take the form of a truncated conical body having a top surface 920 and a bottom surface 930, joined by a substantially continuous side wall 910. The top surface 920 is substantially circular with a diameter that is larger than the diameter of the substantially circular bottom surface 930. As a result, side wall 910 slopes radially inwardly from the top surface 920 toward the bottom surface 930. Although described as substantially continuous, side wall 910 may include a plurality of recesses 940 formed at spaced apart locations along its periphery. Each recess 940 may extend substantially perpendicularly to top surface 920 and bottom surface 930 and may have a substantially rectangular cross-section with a substantially uniform depth along is length.

Figure 10:
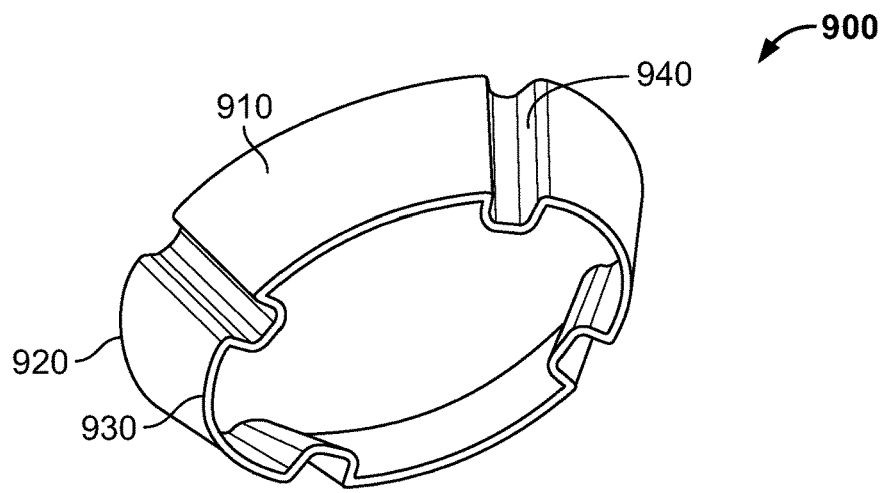
FIG. 10 is a bottom perspective view of the humectant of the packaging system of FIG. 3.

Referring to FIGS. 9-10, the number of recesses 940 in humectant 900 and their positions, dimensions and slope correspond to the number of struts 830 in lid liner 800 and their positions, dimensions and slope. For example, in the illustrated embodiment, lid liner 800 includes four equally spaced struts 830, and humectant 900 includes four equally spaced recesses 940. The width and thickness of each strut 830 are preferably substantially equal to (or slightly less than) the width and depth of each recess 940. Also, the slope of struts 830 preferably is the same as the slope of recesses 940. As a result, humectant 900 may be inserted in lid liner 800 so that struts 830 lie within recess 940 and the portions of side wall 910 between each adjacent pair of recesses 940 protrude into or through the windows 832 of the lid liner. With this arrangement, lid liner 800 is able to hold humectant 900 in place without rotation, while enabling moisture from the humectant to travel downward toward the prosthetic heart valve 10.

It should be understood that the shape, number, and positions of the struts 830 may be varied from the illustrated embodiment, but it is preferable that the humectant 900 be formed with correspondingly shaped and positioned recesses or other features so that the humectant can be supported by lid liner 800 in a stable fashion. As is described in greater detail below, humectant 900 is adapted to provide a desired amount of hydration to the tissues of the valve held in packaging system 300. Thus, although more or fewer struts 830 of different sizes and shapes may be provided in lid liner 800, the resulting window or windows 832 preferably provide enough area through which moisture from the humectant 900 may pass into the portions of packaging system 300 below lid liner 800 when the packaging system is assembled and sealed. Further, although humectant 900 is described as substantially continuous and having a particular shape, the humectant may be provided in any form, including non-continuous forms, that can be stably supported by lid liner 800 or an alternate lid liner that allows the humectant to provide the desired humidity throughout the packaging system 300. In some embodiments, the total area of windows 832 may be at least 25% of the entire surface area of lid liner 800. In other embodiments, the total area of windows 832 may be at least 50% or at least 75% of the entire surface area of lid liner 800.

In one embodiment, humectant 900 is or includes a hydrogel. Hydrogels may be used as water assimilation/absorption agents. They may be formed of cross-linked polymeric networks which are insoluble in water, but which swell to an equilibrium size in the presence of excess water. Polymers are long parallel chains of molecules, and when cross-linked they create a network of polymeric chains. The hydrophilic functional groups attached to the polymeric backbone render hydrogels capable of holding large amounts of water in their networks. Water is brought into the network through the process of osmosis and quickly journeys into the central part of the polymer network, where it is reserved. This is when the hydrogels act as absorbing agents and take on the outward appearance of a gel. Hydrogels can absorb up to 500 times their weight in water, and when their surroundings begin to dry out, the hydrogels gradually dispense up to 95 wt % of their stored water. On the other hand, hydrogels do not dissolve in water due to the cross-links between network chains.

Hydrogels in the present disclosure act as humectants by providing moisture to the tissue portions of the prosthetic heart valve when the humidity inside the packaging system 300 is low, or in other words, when the tissue would otherwise become dry. As noted above, the prosthetic heart valve stored in packaging system 300 may be a wet tissue valve or a dry tissue valve. In some arrangements, the hydrogel within packaging system 300 releases its absorbed water to help ensure that a prosthetic heart valve packaged therein with wet tissue maintains a substantially constant water content of at least about 60 wt % based on the weight of the tissue, preferably about 78.3 wt % in a hydrated form. In other arrangements, the hydrogel releases its absorbed water to hydrate the tissue of a prosthetic heart valve packaged therein in a dried state to maintain a water content of at least about 60 wt % based on the weight of the tissue, preferably about 78.3 wt %.

In some embodiments, humectant 900 is a hydrogel formed from natural sources such as proteins like collagen and gelatin, or polysaccharides like chitosan, dextran and alginate. Hydrogels from natural origins are generally biocompatible and biodegradable, and may contain biological pathogens or evoke an immune response. In other embodiments, humectant 900 is a hydrogel made by polymerization of monomers such as vinyl acetate, acrylamide, acrylic acid and its salts. Synthetic hydrogels have a low risk of biological pathogens to evoke an immune response, but in some circumstances they may have low biodegradability and may contain toxic substances. The water content in humectant 900 may be between about 80 wt % and about 95 wt %, or between about 85 wt % and about 90 wt %.

In one embodiment in which humectant 900 is a hydrogel, at least some of the water in the hydrogel can be replaced with between about 0.05 wt % and about 10 wt % of glutaraldehyde or formaldehyde solution as a preservative. The hydrogel preferably includes between about 0.5 wt % and about 2 wt % of a preservative solution, and more preferably about 1 wt % of such solution. Although the ranges for preservatives provided in this paragraph may be desirable, the amount of preservatives may be greater than the upper ends of the ranges provided. The glutaraldehyde or formaldehyde may help to prevent bacterial growth, allowing the hydrogel to provide both an aseptic environment as well as a humidified environment.

Although lid liner 800 is described above as a single component that acts as both a gasket providing a fluid-tight seal between jar 400 and lid 600 and as a support for humectant 900, these functions may be provided by two separate components. For example, a first structure may be provided that solely functions as a gasket when sandwiched between lid 600 and jar 400. A separate structure with struts and windows similar to lid liner 800 may be provided to support humectant 900. Such separate structure may be operatively coupled to jar 400 or lid 600 in any suitable manner, whether or not coupled to the gasket structure.

In one embodiment, after a prosthetic valve is loaded into jar 400 (with or without any additional support devices such as a valve holder, valve collar 700 or other supports), a gas-permeable sterile barrier 990 is placed over the top opening of jar. The barrier 990 may be glued, heat welded, or otherwise coupled to jar 400. One such gas-permeable sterile barrier is a Tyvek® liner available from E.I. DuPont de Nemours and Company of Wilmington, Del. Preferably, the barrier 990 is not pulled taut over the opening of jar 400, but rather is applied with slack or is otherwise recessed in its center portion. With barrier 990 in place, the contents of jar 400 may be sterilized. In one example, the prosthetic valve and other contents of jar 400 may be sterilized using ethylene oxide ("EtO") sterilization. EtO sterilization may include placing the jar 400, with the gas-permeable sterile barrier in place, under a vacuum and under heat, with EtO vapor passing through the permeable barrier 990 to sterilize the contents of jar 400. A potential downside to the use of EtO sterilization is that the vacuum used during sterilization may dry out the tissue of the prosthetic valve. Another option is peracetic acid ("PAA") sterilization, which is similar to EtO sterilization but may be performed under a less intense vacuum and lower temperatures, which may be less detrimental to the tissue of the prosthetic heart valve.

Figure 11:
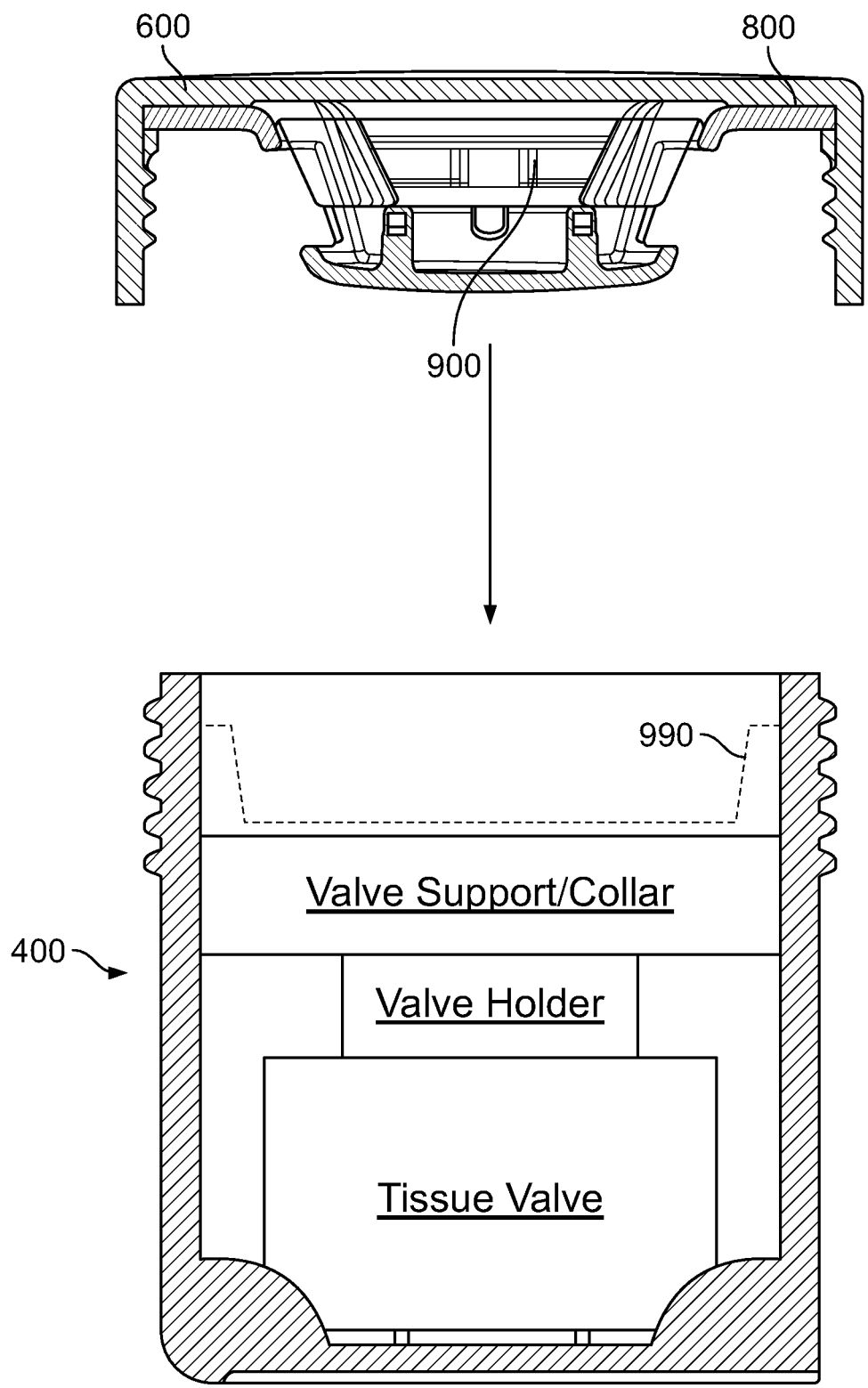
FIG. 11 is a highly schematic view of the valve packaging system of FIG. 3 in the process of being assembled.

Whatever method is used for sterilizing the prosthetic heart valve, the lid 600 and lid liner 800, with humectant 900 supported therebetween, are coupled to the jar 400 after sterilization, preferably with barrier 990 still in place. The assembly process is schematically shown in FIG. 11. As noted above, the barrier 990 preferably has slack or is otherwise recessed so that lid liner 800 and humectant 900 may be accommodated in the space between the barrier and lid 600. Because the barrier 990 is gas-permeable, humectant 900 may provide the desired moisture content throughout the entire closed packaging system 300, on either side of barrier 990, while maintaining the sterility of the prosthetic heart valve. To the extent that the sterilization process dries out the tissue of the prosthetic heart valve, humectant 900 may restore a desired level of hydration to the tissue. Further, if a preservative such as formaldehyde is included in humectant 900, the preservative may help resist any microbial growth within packaging system 300 after the packaging system is sealed and placed in storage. While the humectant 900 may be sterilized using EtO or PAA sterilization, due to the heat and pressure requirements for these methods, particularly for EtO sterilization, it is preferable that the humectant is not subjected to the EtO sterilization process and such process is limited to the components below the barrier 990. If such EtO sterilization of humectant 900 is avoided, it is preferable that a preservative is included in the humectant.

The present disclosure also relates to a method of packaging a tissue valve in the humidor packaging system 300 described above. In one embodiment, the method starts by providing a jar 400, which may or may not contain valve collar 700 and/or additional valve support devices. A tissue valve may be placed in the jar 400 in either a dry state or a hydrated state. The tissue valve may be stabilized by collar 700 and/or any other desired support to keep the valve from significant movement with respect to the jar 400 during storage, transportation, and/or handling. With the valve in place, a sterile gas-permeable barrier 990 may be placed over the open top of the jar 400, and the tissue valve and all contents positioned between the barrier and the inside of the jar may be sterilized. The sterilization may accomplished using any suitable technique, such as EtO or PAA sterilization. Following sterilization, lid 600, lid liner 800, and humectant 900, which may or may not be assembled together before or after the sterilization process, may be attached to jar 400. Humectant 900 includes water and may optionally include a preservative such as formaldehyde. Attaching the lid 600 and lid liner 800 to the jar 400 preferably seals the packaging system in a fluid-tight manner. At least one window 832 may be provided in the lid liner 800 to enable moisture from humectant 900 to permeate the entire interior of packaging system 300. Preferably, humectant 900 maintains the tissue of the tissue valve at a water content of at least about 60 wt %, preferably at about 78.3 wt %. The above-described method may be completed so that, upon sealing the packaging container 300, the tissue valve in not submerged in any significant amount of storage solution, such as aldehyde solution.

According to one aspect of the disclosure, a prosthetic valve packaging system, comprises:

a jar having a closed end, an open end, a side wall, and an interior sized to receive a prosthetic valve therein;

a lid connected to the open end of the jar;

a lid liner having a rim sandwiched between the lid and the side wall of the jar; and a humectant supported within the interior of the jar; and/or a prosthetic valve disposed within the interior of the jar, the prosthetic heart valve including biological tissue; and/or the humectant is in fluid communication with substantially an entirety of the interior of the jar; and/or the lid liner includes a support surface coupled to the rim so that at least one window is defined between the support surface and the rim; and/or the humectant is supported on the support surface of the lid liner; and/or the support surface is coupled to the rim by a plurality of struts spaced apart from one another, the at least one window being defined between an adjacent pair of the struts; and/or the humectant includes a side wall with a plurality of recesses positioned therein, each recess having a shape corresponding to a shape of a corresponding one of the struts; and/or a prosthetic valve disposed within the interior of the jar and a valve support adapted to stabilize the prosthetic valve, the prosthetic valve including biological tissue; and/or a gas permeable sterile barrier interposed between the jar and the lid; and/or the prosthetic valve and the valve support are positioned within the interior of the jar between the bottom of the jar and the gas permeable sterile barrier, and the lid liner and the humectant are positioned between the lid and the gas permeable sterile barrier; and/or the prosthetic valve is not submerged in an aldehyde solution within the interior of the jar; and/or the humectant comprises a hydrogel; and/or the hydrogel has a water content of between about 80 wt % and about 95 wt %; and/or the hydrogel has a water content of between about 85 wt % and about 90 wt %; and/or the hydrogel includes a preservative; and/or the preservative is formaldehyde; and/or the hydrogel has a formaldehyde content of between about 0.5 wt % and about 2 wt %; and/or the hydrogel has a formaldehyde content of about 1 wt %.

According to yet another aspect of the disclosure, a method of packaging a prosthetic valve in a packaging system comprises:

providing a jar having a closed end, an open end, a sidewall and an interior;

positioning the prosthetic valve within the interior of the jar;

positioning a humectant within the interior of the jar; and connecting a lid to the jar to close the open end of the jar, wherein the prosthetic valve is not submerged in a storage solution when the lid is connected to the jar; and/or the step of positioning the humectant within the interior of the jar includes supporting the humectant within the lid; and/or the connecting step includes compressing a compressible seal between the lid and the side wall of the jar to seal the jar in a fluid-tight fashion; and/or coupling a gas permeable barrier to the jar after positioning the prosthetic valve within the interior of the jar, but before positioning the humectant within the interior of the jar; and/or sterilizing the prosthetic valve before positioning the humectant within the interior of the jar; and/or the gas permeable barrier is positioned between the humectant and the prosthetic valve.

Although the invention herein has been described with reference to particular embodiments, it is to be understood that these embodiments are merely illustrative of the principles and applications of the present invention. It is therefore to be understood that numerous modifications may be made to the illustrative embodiments and that other arrangements may be devised without departing from the spirit and scope of the present invention as defined by the appended claims.

The invention claimed is:

1. A method of packaging a prosthetic valve in a packaging system, the method comprising:
   providing a jar having a closed end, an open end, a sidewall and an interior;
   positioning the prosthetic valve within the interior of the jar;
   positioning a humectant within the interior of the jar;
   connecting a lid to the jar to close the open end of the jar; and
   coupling a gas permeable barrier to the jar after positioning the prosthetic valve within the interior of the jar, but before positioning the humectant within the interior of the jar,
   wherein the prosthetic valve is not submerged in a storage solution when the lid is connected to the jar.

2. The method of claim 1, wherein the step of positioning the humectant within the interior of the jar includes supporting the humectant within the lid.

3. The method of claim 1, wherein the connecting step includes compressing a compressible seal between the lid and the side wall of the jar to seal the jar in a fluid-tight fashion.

4. The method of claim 1, further comprising sterilizing the prosthetic valve before positioning the humectant within the interior of the jar.

5. The method of claim 4, wherein the gas permeable barrier is positioned between the humectant and the prosthetic valve.

* * * * *